(12) United States Patent
Galantai et al.

(10) Patent No.: US 8,256,057 B2
(45) Date of Patent: Sep. 4, 2012

(54) PULL THROUGH FOR ENDOSCOPES

(75) Inventors: Ferenc ("Frank") Galantai, Auckland (NZ); Roderick Francis Galantai, Auckland (NZ)

(73) Assignees: Roderick Francis Galantai, Auckland (NZ); Ferenc ("Frank") Galantai, Auckland (NZ); Francis Horton Tuck, Auckland (NZ)

( * ) Notice: Subject to any disclaimer, the term of this patent is extended or adjusted under 35 U.S.C. 154(b) by 793 days.

(21) Appl. No.: 11/920,700

(22) PCT Filed: May 8, 2006

(86) PCT No.: PCT/NZ2006/000098
§ 371 (c)(1),
(2), (4) Date: Nov. 19, 2007

(87) PCT Pub. No.: WO2006/123941
PCT Pub. Date: Nov. 23, 2006

(65) Prior Publication Data
US 2009/0044353 A1      Feb. 19, 2009

(30) Foreign Application Priority Data
May 17, 2005   (NZ) .......................... 540125

(51) Int. Cl.
*B08B 9/027*      (2006.01)

(52) U.S. Cl. .................. 15/104.16; 15/104.05

(58) Field of Classification Search ............... 15/104.16, 15/104.2, 104.05, 211
See application file for complete search history.

(56) References Cited

U.S. PATENT DOCUMENTS

| | | | | |
|---|---|---|---|---|
| 4,715,747 A | * | 12/1987 | Behrens | 405/303 |
| 4,962,607 A | * | 10/1990 | Baldwin | 42/95 |
| 5,964,004 A | | 10/1999 | Bean | |
| 6,088,866 A | * | 7/2000 | Hedge | 15/104.16 |

FOREIGN PATENT DOCUMENTS

| | | |
|---|---|---|
| WO | WO 00/10476 | 3/2000 |
| WO | WO 01/28406 | 4/2001 |

OTHER PUBLICATIONS

Saunders et al., "A Selective uranium extraction agent prepared by polymer imprinting," Chem. Commun. pp. 273-274 (2000).

* cited by examiner

*Primary Examiner* — Randall Chin
(74) *Attorney, Agent, or Firm* — Jacobson Holman PLLC

(57) ABSTRACT

A pull through having a filament about which, at least in part, there is carried at least one mass to fulfil a cleaning role, wherein said mass defines a sheath at least in part on the filament and at least two radial fins (A) integral with and/or carried by the sheath or extension thereof, and (B) axially spaced with respect to the sheath axis and the filament axis, and wherein said fins are each substantially radially directed with respect to said axes axis yet are of a profile and are formed in a material such that each, without any substantial interference of the other, can assume a configuration for a conduit to be cleaned smaller than that notionally just touchable by the undeformed fins.

23 Claims, 2 Drawing Sheets

DETAIL A
SCALE 8 : 1

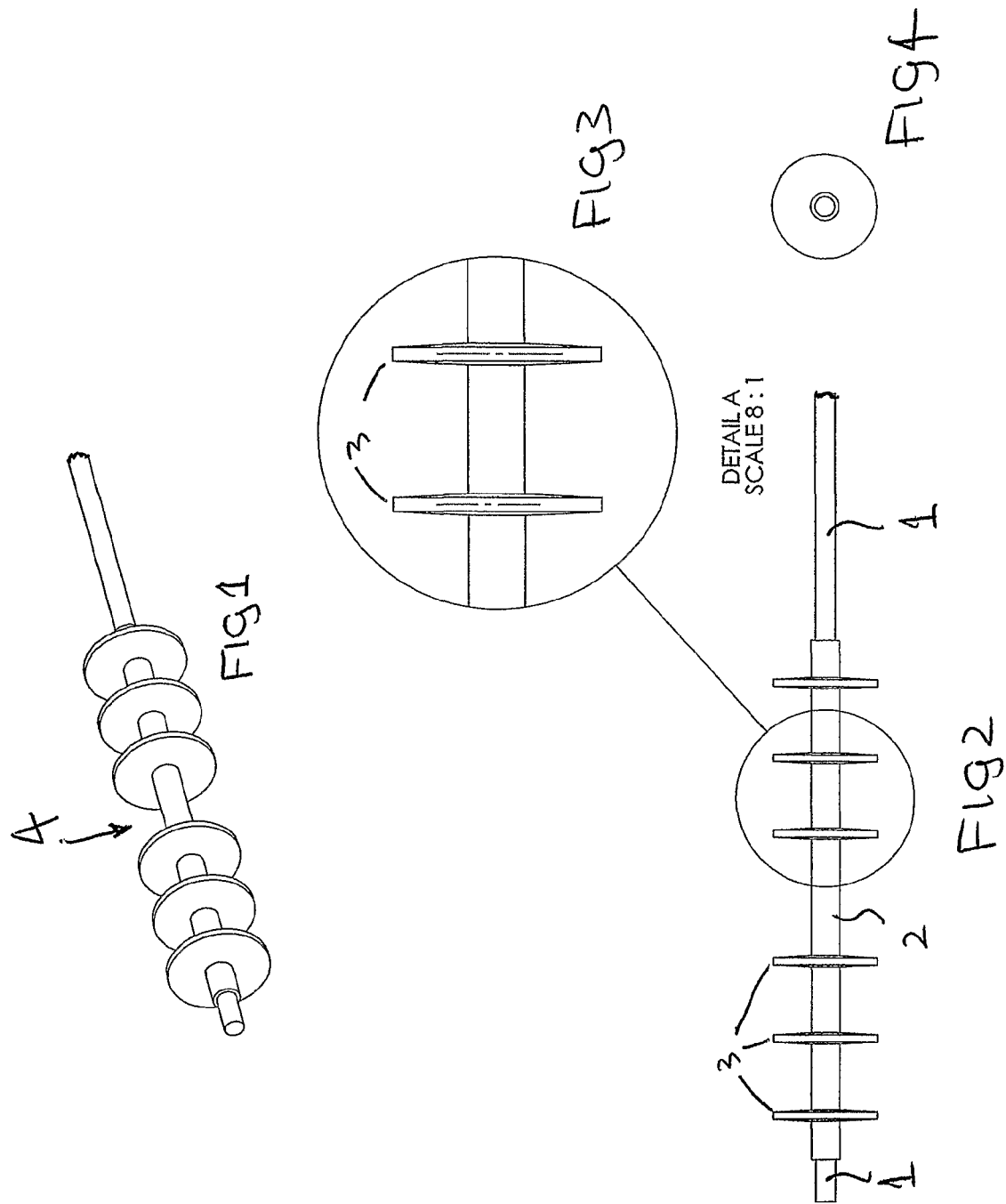

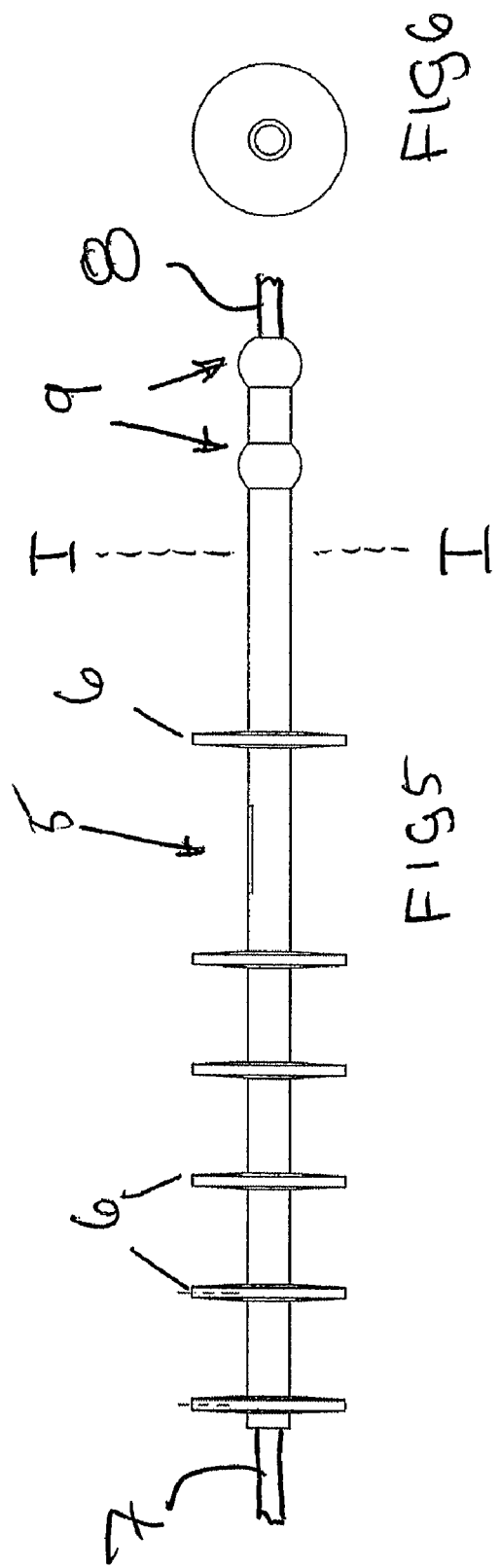
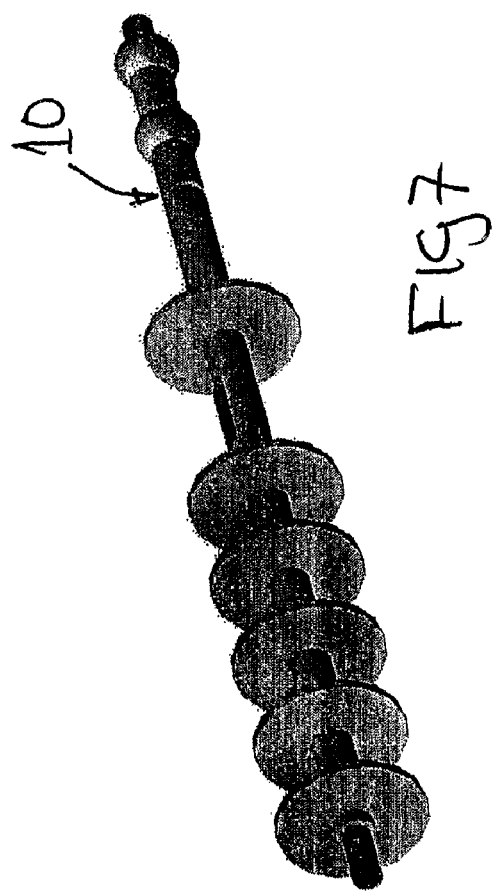

PULL THROUGH FOR ENDOSCOPES

This is a national stage of International application of PCT/NZ2006/000098 filed on May 8, 2006 and published in English.

TECHNICAL FIELD

The present invention relates to pull throughs such as those suitable for cleaning endoscopes.

BACKGROUND ART

Endoscopes require frequent cleaning. It is found that endoscopes (such as those lined with, for example, a polyurethane sleeve) can be sterilised between uses by a cleaning regime that involves the pushing and/or pulling through of a brush or other cleaning head, the effect of which is to smooth the inwardly directed surface and surface deposits of the polyurethane sleeve or its equivalent. Apparently this better enables chemical cleaning and sterilisation to ensure. See for example the post 2 Mar. 2000 published content of PCT/AU99/00669 (WO00/10476) of Novapharm Research (Australia) Pty Limited, the full content of which is here included by way of reference.

A feature of the pull through of aforementioned WO00/10476 is the requirement that the cleaning member at the end of the pull through be 0.1 mm narrower than the passageway of the endoscope to be cleaned.

PCT/NZ00/00198 (published as WO01/28406) of Galantai (Plastics) Group Limited discloses a pull through manufacturing process where the pull through is suitable for cleaning endoscopes. The pull through is manufactured reliant upon a filament having at least a thermoplastic surface and a moulded thermoplastic mass about the filament defining a pull through profile adapted for the purpose of the pull through. The filament is preferably a monofilament sufficiently stiff to enable its threading through a conduit, passageway or the like of an endoscope for which it is adapted or intended for use. The moulded thermoplastic mass (i.e. the pull through profile or cleaning feature) is of a material of lower melting point than at least part of the filament.

A feature of the manufacturing procedure of a pull through of WO01/28406 is the conditioning of the coil or spool fed filament at an elevated temperature whilst under axial tension so as to reduce coil or spool memory in the filament. This better enables a manufacturing procedure whereby substantially straight pull throughs can be accumulated for packaging or other downstream treatment.

The cleaning profile, mass or head of WO01/28406 involved a materials blend and outstanding 360° fins requiring matching of the pull through to specific endoscope channel sizes.

U.S. Pat. No. 5,964,004 of DC Bean describes an endoscopic tube cleaner where the body of the cleaner extends axially in relation to the tube with a plurality of blades integral with the body. A feature of that particular arrangement is the provision whereby each blade of an axially spaced set of such blades is such that there is 360° wiping but each blade itself does not provide for 360° wiping. This may enable some adaptability to different endoscope channel sizes. U.S. Pat. No. 5,964,004 states that the invention is directed to a system where the user must be absolutely certain that every portion of the inside surface of the endoscopic tube has been wiped by the blades. This they state is accommodated where, unlike prior art where blades or their equivalent each wipe the entire circumference internally of the tube, their blades do not each subtend 360° about the axis of the body i.e. as stated in the claim set "at least one of said blades provided at each of first and subsequent axially spaced locations lengthwise on the body" "are rotationally staggered in their angular placement around the axis of the body so that when the tube cleaner is viewed in the axial direction, the at least one gap in the area of the walls not contacted and wiped by said at least one of said blades at the first location is completely covered by the immediately adjacent said at least one of said blades at the next subsequent axially spaced location".

The present invention is directed, in one aspect, to cleaning apparatus such as an endoscopic pull through with adaptability to accommodate different size circular conduits (e.g. endoscopic conduits, channels, passageways or the like ("channels")) such that the one size can effectively accommodate the cleaning requirement of each of a range of endoscopic channel diameters.

For example, whilst the Olympus™ endotherapy devices have a range of minimum channel diameters vis 1.2 mm, 1.7 mm, 2.0 mm, 2.6 mm, 2.8 mm, 3.7 mm, 5.0 mm and 6.0 mm, commonly used channel diameters are, say, 5.0 mm and 2.6 mm. Likewise whether the endoscope brand is that of Pentax™ or other providers.

The invention, in an alternative aspect, is directed to a manufacturing process suitable for pull through production.

DISCLOSURE OF INVENTION

In one aspect the invention is a pull through suitable for cleaning a channel of, for example, an endoscope, the pull through having a filament about which, at least in part, there is carried at least one mass to fulfil a cleaning role, said mass defining a sheath at least in part on the filament and at least two radial fins integral with and/or carried by the sheath (or extension thereof) and axially spaced with respect to the sheath and filament axis, wherein said fins are each substantially radially directed with respect to said axial axis yet are of a profile, are spaced and formed in a material whereby each fin without any substantial interference of the other can clean a conduit of about the fin diameter and/or a conduit having a diameter more than 1 mm smaller than that of the fin diameter preferably more than 1.5 mm smaller than that of the fin diameter and most preferably at least 2 mm smaller than that of the fin diameter.

Preferably the material is a TPE, TPR, TPU or TPV. Preferably the material is a TPE such as TPV.

Preferably said fins are adapted to be useable in at least two diameter channels which may vary by greater than 1 mm in diameter [preferably at least 1.5 mm diameter variance and most preferably at least 2 mm diameter difference (e.g. about 5 mm and 2.6 mm diameters which are diameters with a differential of 2.4 mm)].

Preferably the material has a Shore A Hardness in the range of from 45 to 75. Preferably said Shore A Hardness is about 60.

Preferably the material has a flexural yield and flex modulus typified by that of the TPE (it is a TPV) SANTOPRENE (a trade mark of Advanced Elastomer Systems, L.P). A suitable SANTOPRENE grade is SANTOPRENE rubber 201-64W175.

Preferably the fin diameter is about 5.2 mm.

Preferably the fins have a thickness less than 0.7 mm (preferably less than 0.6 mm).

Preferably the fins fine down to their circumference by about 0.2 mm.

Preferably the fin spacing is in a ratio of spacing to fin diameter of from 0.6:1 to 0.85:1 [preferably about 0.73:1 (e.g. 3.8 mm spacing for about a 5.2 mm diameter)].

In another aspect the invention is a pull through (preferably sterilisable) suitable for cleaning a circular or near circular channel of, for example, an endoscope, the pull through having a filament about which, at least in part, there is carried at least one mass to fulfil a cleaning role, said mass defining a sheath at least in part on the filament and at least two radial fins, integral with and/or carried by the sheath (or extension thereof), axially spaced with respect to the sheath and filament axis, wherein said fins are each substantially radially directed with respect to said axial axis yet are of a profile and are spaced and formed in a material [preferably selected from the group consisting of TPE, TPR, TPU and TPV] such that each, without any substantial interference of the other, can assume a configuration for a conduit, say, in the range of from 4 to 5.5 mm diameter to be cleaned and/or a conduit, say, in the range of from 2 to 3.5 mm diameter.

Preferably the sheath is of about 1.4 mm diameter on an about 1 mm diameter filament.

Preferably the material is a TPE (e.g. a TPV). Preferably it is as aforesaid.

Preferably the profile can clean a profile of diameter about 5 mm and a profile of diameter between 2 and 3 mm.

Preferably the fin diameter is about 5.2 mm.

Preferably the fins have a thickness less than 0.7 mm (preferably less than 0.6 mm).

Preferably the fins fine down to their circumference by about 0.2 mm.

Preferably the fin spacing is in a ratio of spacing to fin diameter of from 0.6:1 to 0.85:1 [preferably about 0.73:1 (e.g. 3.8 nm spacing for about a 5.2 mm diameter)].

In another aspect the invention is a pull through suitable for cleaning a circular or near circular channel of, for example, an endoscope, the pull through having a filament about which, at least in part, there is carried at least one mass to fulfil a cleaning role, said mass defining a sheath at least in part on the filament and at least two radial fins, integral with and/or carried by the sheath (or extension thereof) axially spaced with respect to the sheath and filament axis, wherein said fins are each substantially radially directed with respect to said axial axis yet are of a profile, are spaced and formed in a material whereby each fin without any substantial interference of the other can clean a conduit of about the fin diameter and/or a conduit greater than 1 mm diameter smaller (preferably greater than 1.5 mm Ø smaller), [most preferably at least 2 mm Ø smaller].

Preferably the fin diameter is about 5.2 mm.

Preferably the fins have a thickness less than 0.7 mm (preferably less than 0.6 mm).

Preferably the fins fine down to their circumference by about 0.2 mm.

Preferably the fin spacing is in a ratio of spacing to fin diameter of from 0.6:1 to 0.85:1 [preferably about 0.73:1 (e.g. 3.8 mm spacing for about a 5.2 mm diameter)].

In another aspect the invention consists in an endoscope or the like channel pull through cleaner made in circumstances where a filament intermittently, continuously or otherwise drawn through a moulding zone has had a profiled mass moulded thereon and the profiled mass and the filament has then been substantially transversely cut, or otherwise separated, to define with part of the mass carried by one filament length a pull through cleaning profile for a pull through and with another part of the mass carried by another filament length a feed in profile for a pull through.

The resulting pull throughs preferably are identical i.e. the moulding repeats.

Preferably the fin diameter is about 5.2 mm.

Preferably the fins have a thickness less than 0.7 mm (preferably less than 0.6 mm).

Preferably the fins fine down to their circumference by about 0.2 mm.

Preferably the fin spacing is in a ratio of spacing to fin diameter of from 0.6:1 to 0.85:1 [preferably about 0.73:1 (e.g. 3.8 mm spacing for about a 5.2 mm diameter)].

In another aspect the present invention consists in an endoscope or the like channel pull through cleaner as aforesaid that is also a pull through as previously defined and/or uses the technology disclosed in the Galantai specification WO01/28406.

In another aspect the present invention consists in a method of manufacture as in the aforementioned Galantai specification when producing pull throughs and/or endoscope or the like channel pull through cleaners in accordance with the present invention.

As used herein the terms "TPE", "TPR", "TPU" and "TPV" refer to thermoplastic elastomers, rubbers, urethanes and vulcanisables respectively.

As used herein "sheath" includes sleave and any alternative thereto.

BRIEF DESCRIPTION OF DRAWINGS

A preferred form of the present invention will now be described with reference to the accompanying drawings in which FIG. 1 is a perspective view of a cleaning profile of one embodiment to the present invention, FIG. 2 is a side elevational view of the arrangement shown in FIG. 1, FIG. 3 is an enlargement of two of the annular disc like fins of the cleaning profile of FIGS. 1 and 2, FIG. 4 is an end view from either end of the arrangement shown in FIG. 2, FIG. 5 is a view showing a continuous filament having moulded thereon a moulded form to be cleaved, cut or otherwise separated along the line II so as to provide to the left of II a cleaning profile of one pull through and to the right of the line II a lead in feature for another pull through, FIG. 6 is an end view from the left of the arrangement shown in FIG. 5, and FIG. 7 is a perspective view of the embodiment shown in FIGS. 5 and 6.

Preferably the manufacturing procedure involves a moulded arrangement as depicted in FIGS. 5 through 7 yet provides a variation of a cleaning form to that depicted in FIGS. 1 through 4 i.e. can be of any suitable form such as that depicted to the left of II of FIG. 5.

The manufacturing procedure can be any suitable procedure but is preferably as hitherto disclosed in the aforementioned Galantai specification WO01/28406). The filament material is preferably any of the options disclosed therein (e.g. PP) (more preferably PP with a blowing agent as discussed in WO01/28406).

FIG. 2 shows a filament 1 of, for example, (polypropylene, nylon or the like) having moulded thereon a sheave 2 having two sets of three fins 3 (or, not shown, a more preferred form of a set of two fins and a set of three fins) each of which is spaced and rendered sufficiently flexible by virtue of the sheath, its material and its contour as to satisfy the requirements.

The sheave thickness was relatively thin but is sufficient to provide grip on the monofilament 1 for the moulded mass shown or as shown in FIGS. 5 to 7.

By way of example, if the monofilament is 1 mm in diameter a filament that is approximately 1.4 mm in diameter is sufficient to provide an appropriate anchor for the fins which could be of about 5.2 mm diameter.

The fins preferably angle so as to taper to their outer extremity i.e. the circumference from about 0.55 mm thick to about 0.35 mm thick. The injection point for a product as shown in FIGS. 1 through 4 can be at 4.

For the arrangement as shown in FIGS. 5 through 7 the injection point can be at 5 and the fins 6 can be provided in some form of asymmetry but preferably with similar dimensions for each fin and the sheath as defined previously. Shown in FIG. 5 is the filament 7 to be part of a first or second pull through and a monofilament region 8 to be part of a second or first pull through, the separation being on line II so as to provide a lead in beading or the like 9.

Means can be provided to facilitate cleavage by an appropriate knife or other separating means at 10 which is on the axis II. A person skilled in the art will appreciate that the beaded part for the lead in can be of, for example, a radius of about 1.05 mm.

The moulded mass as shown in FIG. 5 for example 37.52 mm long but with the more regular spacings of the fins being about 3.8 mm. The dimensions are otherwise as mentioned with respect to the other embodiment.

With such preferred embodiments with the moulded mass, form or profile of a SANTOPRENE rubber as aforesaid and dimensions as discussed, it can be pulled through the channel of an endoscope having a nominal diameter of 5 mm as well as a channel having a nominal diameter in the range of 2 to 3 mm e.g. 2.6 mm.

A person skilled in the art will appreciate how, depending on the deformation history of the material, the product can be made for a single use only such that once used through a narrow conduit it is less appropriate for it to be reused in a larger channel. In other forms however it can be modified so as to be sterilisable and reusable.

A person skilled in the art will appreciate the options that a pull through of the present invention provides for the advantages previously stated from a manufacturing point of view and/or flexibility of use point of view.

Persons will also appreciate that a product as aforesaid can provide very effective cleaning with actual contact always with the material on the surfaces to be cleaned.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The invention claimed is:

1. A lumen pull through for an endoscope, the lumen pull through comprising
    a filament, and
    a profiled mass dependent from the filament, the profiled mass including a sheath at least in part on the filament and at least three directly adjacent fully circumferential radial fins of an at least approximately equal diameter carried by the sheath, the radial fins being axially spaced with respect to an axis of both the sheath and the filament, thereby providing at least two pairs of adjacent ones of said fully circumferential radial fins,
    said radial fins being each substantially radially directed with respect to said axis of said sheath and the filament, and being of a profile, mutual spacing and formed in a material so that each of said radial fins, without any substantial interference between the radial fins upon deflection, cleans an endoscope at least 1 mm in diameter smaller than a diameter of the radial fins by having said mutual spacing between said radial fins being greater than a radial distance of said fins extending from said sheath, said mutual spacing being between the adjacent fins of each of said at least two pairs of fully circumferential adjacent radial fins.

2. The pull through of claim 1, wherein the sheath and fin material is a TPE, TPR, TPU or TPV.

3. The pull through of claim 1, wherein each fin has a substantially circular periphery about coincident sheath and filament axes.

4. The pull through of claim 1, wherein the sheath is of about 1.4 mm diameter on an about 1 mm diameter filament.

5. The pull through of claim 1, wherein the fin diameter is about 5.2 mm.

6. The pull through of claim 5, wherein the fins are gradually reduced in thickness at a perimeter circumference by about 0.2 mm.

7. The pull through of claim 1, wherein the fins have a thickness less than 0.7 mm.

8. The pull through of claim 7, wherein the fins have a thickness less than 0.6 mm.

9. The pull through of claim 1, wherein the fin spacing is in a ratio of spacing to fin diameter of from 0.6:1 to 0.85:1.

10. The pull through of claim 9, wherein the ratio is about 0.73:1.

11. The pull through of claim 1, wherein the fin separation is 3.8 mm spacing for about 5.2 mm diameter fins.

12. The pull through of claim 1, wherein the profiled mass material has a Shore A Hardness in the range of from 45 to 75.

13. The pull through of claim 12, wherein said Shore A Hardness is about 60.

14. The pull through of claim 1, wherein the profiled mass material has a flexural yield and flex modulus of a TPV.

15. The pull through of claim 1, wherein there are more than two fully circumferential radial fins of an at least approximately equal diameter.

16. The pull through of claim 15, wherein the fin spacing of adjacent fins is equal.

17. The pull through of claim 15, wherein the fin spacing is asymmetric along the sheath.

18. The pull through of claim 1, wherein the radial fins are greater than 5 mm in diameter.

19. The pull through of claim 18, wherein the radial fins are about 5.2 mm in diameter.

20. The pull through of claim 19, wherein a fin spacing between two adjacent radial fins is about 3.8 mm.

21. The pull through of claim 1, wherein each adjacent pair of fins has a fin spacing in a ratio of spacing to fin diameter of from 0.6:1 to 0.85:1, each fin is at least 5 mm in diameter, and each fin is thicker near the sheath than at a circumference.

22. The pull through of claim 1, wherein said mutual spacing is between every two adjacent ones of said radial fins.

23. The pull through of claim 1, wherein two said pairs of adjacent fins include a fin common to each pair.

* * * * *